United States Patent [19]

Beauford et al.

[11] Patent Number: 4,661,157

[45] Date of Patent: Apr. 28, 1987

[54] PRODUCTION OF SHAPED BODIES OF BORON COMPOUNDS

[75] Inventors: William Beauford, South Barrow Nr. Yeovil; Nicholas J. Spragg, Bourton; Malcolm Millar, Widnes, all of England

[73] Assignee: Laporte Industries Limited, London, England

[21] Appl. No.: 796,921

[22] Filed: Nov. 12, 1985

[30] Foreign Application Priority Data

Nov. 21, 1984 [GB] United Kingdom ............... 8429447

[51] Int. Cl.$^4$ ..................... A01N 25/34; C08K 3/38
[52] U.S. Cl. .................. 106/18.13; 106/18.3; 423/276; 423/280; 424/148
[58] Field of Search ............. 424/148; 423/276, 277, 423/278, 279, 280; 149/22; 106/18.13, 18.3

[56] References Cited

U.S. PATENT DOCUMENTS

| | | | |
|---|---|---|---|
| 1,961,073 | 5/1934 | Newman | 423/280 |
| 2,886,425 | 5/1959 | Seibert | 423/280 |
| 2,957,749 | 10/1960 | Reburn et al. | 423/280 |
| 2,983,577 | 5/1961 | Morgan | 423/280 |
| 3,300,278 | 1/1967 | Nies et al. | 423/280 |
| 4,061,512 | 12/1977 | Chew et al. | 149/22 |

FOREIGN PATENT DOCUMENTS

| | | | |
|---|---|---|---|
| 2008640 | 6/1979 | United Kingdom | 106/18.13 |
| 2114003 | 8/1983 | United Kingdom | 106/18.13 |

*Primary Examiner*—Ronald W. Griffin
*Attorney, Agent, or Firm*—Kane, Dalsimer, Kane, Sullivan and Kurucz

[57] ABSTRACT

Boron compounds such as alkali metal or alkaline earth metal borates capable of forming hydrates or higher hydrates may be formed into shaped bodies by forming into a paste with water and allowing the water to be bound to form a solid shaped body. The bodies are useful as inserts into preformed cavities in structures, e.g. of wood, liable to insect, fungal or other infestation by virtue of the slow dissolution of the insert and the toxicity to such organisms of the boron compounds.

10 Claims, No Drawings

PRODUCTION OF SHAPED BODIES OF BORON COMPOUNDS

This invention relates to the production of shaped bodies of boron compounds having fungicidal, insecticidal or other biocidal effect and their use in the treatment of structures for example timber or masonry to combat fungal, insect or other infestation therein.

United Kingdom Patent Specification No. 2008640A of Wood-Slimp GmbH relates to the treatment of structures of timber in the form, for example, of railway sleepers, door and window frames, bridges and boats, by locating in a cavity in the timber an insert comprising a shaped, fused body of boric oxide which dissolves over an extended period in moisture present in the timber to form a solution toxic to the organisms responsible for the decay of timber. Such a body is disclosed to be made by extrusion of the boric oxide in the molten state or by moulding and compacting particulate boric oxide and then fusing it by heat to form monolithic structures. Boric oxide glass softens at a temperature of 325° C. and requires melt extrusion temperatures considerably in excess of this. The use of melt extrusion causes practical processing problems. The alternative process of moulding compacting and then fusing particulate boric oxide is disclosed to be preferred in the specification referred to.

United Kingdom Patent Specification No. 2114003 of Bio-Kil Laboratories Limited relates to the treatment of structures of timber, masonry or the like by locating in a cavity in the structure a tablet comprising a mixture of particulate boron compounds, selected from at least two of the three groups of borates, boric acids and boric oxides, and a binder, the tablet being shaped by compaction under pressure.

The present invention provides a new or improved process for the production of shaped bodies of boron compounds which requires neither high temperatures nor high pressures and is readily operable continuously or semicontinuously. The Applicants have discovered that many boron compounds, even those already in the form of hydrates can bind a quantity of water and that this effect can be utilised in the production of shaped bodies suitable for use for the treatment of structures with the boron compounds.

The present invention provides a process for the production of a shaped body, comprising one or more boron compounds, suitable for use as a preservative insert in structures liable to biological attack, characterised by forming a paste comprising water and one or more boron compounds capable of binding water by hydration, shaping the paste and allowing the shaped paste to solidify by the binding of at least a portion of the water therein to form the shaped body. It is believed that the paste solidifies by the formation of a crystalline hydrate, or a higher hydrate, of the boron compound.

The shaped body so produced often forms a homogenous monolithic structure different in character both from pressure compacted tablets and from fused structures.

The selection of suitable boron compounds for use according to this invention may be made on the basis of a theoretical knowledge of their ability to bind water and/or on the basis of a practical test conducted by mixing a small quantity, for example 100 g of the solid, with a restricted quantity of water to form a paste and observing whether the paste solidifies without drying.

For practical use according to the invention the paste is preferably of shapable consistency and solidifies in a time which is compatible with the operational speed of the mixing and shaping equipment used. The speed of solidification also affects the physical strength of the shaped product. Boric oxide, for example, binds water very rapidly and with a considerable evolution of heat and is difficult to shape and gives structurally weak bodies. Orthoboric acid binds water relatively slowly and without any appreciable evolution of heat and again gives structurally weak bodies. These two compounds are therefore not preferred for use according to this invention and are preferably either absent or are present in a minor proportion only for example, particularly preferably, below 20% by weight of the paste. Preferably the boron compounds are selected from alkali metal or alkaline earth metal borates.

As a practical guide to the selection of suitable boron compounds capable of binding water, and without limiting the invention thereto, boron compounds which, when 500 g thereof is mixed with 20% of water, by weight of the boron compound and water, develop a temperature of from 35° C. to 90° C. preferably 40°0 C. to 75° C. from ½ to 10 minutes, are suitably utilised. Under such a test disodium octaborate tetrahydrate, which is a preferred boron compound herein, develops a temperature of about 50° C. in about 5 minutes.

To achieve satisfactory shaping the quantity of water should generally be within the limits of 15% and 35% by weight of the composition to be shaped. A preferred lower quantity of water is 20% by weight. Above about 30%, and particularly above 35%, by weight of water there will be a tendency for an increasing quantity of water to remain, in the unbound state, in the shaped product as evidenced by a gradual loss of weight in storage. This is not unduly disadvantageous so long as such unbound water does not lead to evident dampness or stickiness in the product or an unduly long solidification time. Even at the extreme limits, however, the quantity of unbound water in the product should be less than 10% by weight. It is understood therefore that, depending on the particular formulation it might be possible to obtain advantage from the invention using a quantity of water outside the limits of 15% and 35% by weight, for example from 12% to less than 15% or from greater than 35% to 37% or even 40% by weight of the composition to be shaped although operation at these extreme limits is generally not preferred.

It may be desired to modify the properties of the shaped product by the use of additives. The addition of alkali metal oxides may be used to increase the rate of solution and the addition of alkaline earth metal or silicon oxides to reduce the rate of solution of the boron compounds in water, and such additives may be included in the paste to be shaped according to this invention. Metal compounds, such as, for example, copper oxide or copper borate may be used for their toxicity to fungal or insect infestations. Cements such as calcium sulphate hemihydrate (Plaster of Paris) may be used to increase the physical strength of the shaped product. Thixotropic agents such as natural or synthetic swelling clays may be used to increase the integrity of the shaped paste prior to solidification. Preferably additives are present in less than 10% by weight and particularly preferably in less than 5% by weight of the final solid composition although copper borate, because of its ability to hydrate and its boron content, may be used in a larger quantity as part, or even all, of the boron compound. Non-aqueous liquid additives, if present, are preferably in less than 5%, particularly preferably in less than 3% by weight of the final solid composition since the presence of any larger quantity could adversely effect the solidification process.

It is a further feature of this invention that other solid materials may readily be included in the shaped solid product.

It may be advantageous to utilise mixtures of solid boron compounds having different rates of dissolution such as boric oxide glass or fused disodium octaborate with a non-fused boron compound capable of binding water such as an alkali metal borate. It has been found that the shaped solid product of the present invention provides a suitable carrier or binder for such other materials not themselves capable of contributing to the solidification process which may be dispersed throughout the paste to be shaped as powder or as lumps consistent with their size not adversely affecting the shaping process. Alternatively, if desired, a central core of such other material may be included within the solid shaped compositions by for example, reverse extrusion of the latter about the core. Such non-homogenous products are particularly useful in that they provide differential treatment as a result of a relatively rapid initial dissolution of one portion of the product followed by a relatively slow dissolution of the other portion.

If desired the products of this invention may be shaped by filling the paste into water permeable containers, for example cylinders, and allowed to set therein. This provides further means for controlling the rate of dissolution, for example by utilising a multilayer cardboard or paper container of desired water permeability or a plastic container having a desired number of apertures to control the rate of ingress of water.

The products of this invention may be produced by extrusion using a continuously operable mixer/extruder such as the twin-screw GB2 model, for example, of the Baker Perkins Company. The extrudates produced may be received onto a conveyor on which they may conveniently be separated into lengths of, for example, 1 meter in which form they may be stored until fully solidified and then divided into the required lengths for use, for example, into lengths of 5 mm upwards. A suitable diameter may be, for example, from 5 mm upwards. Such division of the fully solidified product may be by means of a saw, or by breakage following an initial saw nick. Alternatively the extrudates may be marked for later breakage, or cut, as extruded and before solidification.

In the course of the solidification process heat is evolved both in the mixer and in the extrusion section of the apparatus. It has been found of advantage to control this heat by cooling the extrusion section and, if necessary, the mixing section to prevent the temperature in the mixing and extrusion sections exceeding, preferably, 90° C., particularly preferably 70° C., and heating the die section. Preferably the temperature in the die section is greater than that in the extrusion section by greater than 5° C. preferably greater than 10° C. Control in this manner helps to improve the ease of extrusion and the surface quality of the extrudates.

Using the above-mentioned techniques disodium octaborate tetrahydrate was mixed with water in a 75:25 weight ratio and extruded through an 18 mm die maintaining the extrusion section temperature below 70° C. by external water cooling. The extrudate was received onto a conveyor through a die heated to above 80° C., divided into 1 meter lengths, allowed to solidify and sawn into 10 cm lengths. The extrudates were cylindrical in shape and had not sagged appreciably after extrusion and had a smooth outer surface, due to the differential extrusion temperature, and a dense homogenous consistency. Such a product is suitable for use as an insert in the preservation of structures of e.g. timber or masonry.

We claim:

1. A process for the production of a shaped body, comprising one or more boron compounds, suitable for use as a preservative insert in structures liable to biological attack, characterised by forming a paste comprising water and one or more boron compounds capable of binding water by hydration, shaping the paste and allowing the shaped paste to solidify by the binding of at least a portion of the water therein to form the shaped body.

2. A process as claimed in claim 1 wherein the one or more boron compounds are selected from alkali metal and alkaline earth metal borates.

3. A process as claimed in claim 2 wherein said one or more boron compounds comprise disodium octaborate tetrahydrate.

4. A process as claimed in claim 1 wherein there is also included in the paste fused particles of one or more boron compounds.

5. A process as claimed in claim 1 wherein the paste is shaped by extrusion.

6. A process as claimed in claim 5 wherein the die section of the extruder is maintained at a temperature greater than tha of the preceding extrusion section thereof.

7. A process as claimed in claim 6 wherein the die section is heated and the preceding extrusion section is cooled 8. A shaped body suitable for use as a preservative insert in structures liable to biological attack comprising particles of one or more boron compounds bound by crystallisation.

9. A shaped body as claimed in claim 8 also including fused particles of one or more boron compounds.

10. A method for preserving a structure liable to biological attack comprising forming a cavity in the body and locating in the cavity a shaped body as claimed in claim 8.

* * * * *